(12) United States Patent
Goralczyk et al.

(10) Patent No.: US 8,759,405 B2
(45) Date of Patent: Jun. 24, 2014

(54) STEVIA EXTRACT OR STEVIOL FOR HAIR CARE

(75) Inventors: Regina Goralczyk, Grenzach-Wyhlen (DE); Annis O. Mayne-Mechan, Moehlin (CH); Jenny Piussi, Schliengen (DE); Henry Rieger, Grenzach-Wyhlen (DE); Hasan Mohajeri, Egg b. Zuerich (CH)

(73) Assignee: DSM IP Assets B.V., Heerlen (NL)

( * ) Notice: Subject to any disclaimer, the term of this patent is extended or adjusted under 35 U.S.C. 154(b) by 116 days.

(21) Appl. No.: 13/386,469

(22) PCT Filed: Jul. 20, 2010

(86) PCT No.: PCT/EP2010/060487
§ 371 (c)(1),
(2), (4) Date: Apr. 6, 2012

(87) PCT Pub. No.: WO2011/009863
PCT Pub. Date: Jan. 27, 2011

(65) Prior Publication Data
US 2012/0184500 A1 Jul. 19, 2012

(30) Foreign Application Priority Data
Jul. 21, 2009 (EP) .................................... 09166022

(51) Int. Cl.
*A61K 31/015* (2006.01)
(52) U.S. Cl.
USPC ........................................................ 514/766
(58) Field of Classification Search
USPC ................................. 514/25, 766
See application file for complete search history.

(56) References Cited

U.S. PATENT DOCUMENTS

| 2003/0152655 A1* | 8/2003 | Grallert .................... 424/757 |
| 2007/0009638 A1 | 1/2007 | Takemori et al. |
| 2007/0254946 A1 | 11/2007 | Nakaoji et al. |

FOREIGN PATENT DOCUMENTS

| EP | 1 666 036 | 6/2006 |
| EP | 1 673 986 | 6/2006 |
| WO | WO 01/58414 | 8/2001 |

OTHER PUBLICATIONS

Maki et al, "Chronic consumption of rebaudioide A, a steviol glycoside, in men and women with type 2 dibetes mellitus", Food and Chemical Toxicology, vol. 46 (2008), pp. S47-S53.*
Chatsudthipong et al, "Stevioside and related compounds: Therapeutic benefits beyong sweetness", Pharmacology & Therapeutics.*
International Search Report for PCT/EP2010/060487, mailed Jun. 16, 2010.
Written Opinion for PCT/EP2010/060487, mailed Jun. 16, 2010.

* cited by examiner

*Primary Examiner* — Elli Peselev
(74) *Attorney, Agent, or Firm* — Nixon & Vanderhye P.C.

(57) ABSTRACT

Methods of enhancing the appearance of a mammal's hair/fur are provided by the administration of an oral nutraceutical or food composition comprising steviol or a steviol precursor, without chromene, for a time sufficient and in an amount effective to enhance the overall appearance of the mammal's hair/fur. The enhancement of the appearance of the mammal's hair/fur includes restoring hair/fur color, lessening hair loss, increasing the thickness of hair, counteracting age-associated hair thinning, and delaying the onset or severity of age-associated hair loss and thinning. A nutraceutical or food which includes steviol or a steviol precursor in an amount sufficient to enhance the overall appearance of a mammal's hair/fur is also provided.

4 Claims, 4 Drawing Sheets

STEVIA EXTRACT OR STEVIOL FOR HAIR CARE

This application is the U.S. national phase of International Application No. PCT/EP2010/060487 filed 20 Jul. 2010 which designated the U.S. and claims priority to EP Patent Application No. 09166022.5 filed 21 Jul. 2009, the entire contents of each of which are hereby incorporated by reference.

FIELD OF THE INVENTION

This invention relates to the use of an oral composition comprising *Stevia* extract, steviol precursors (steviol glycosides), or free steviol which enhances the appearance of hair and counteracts hair loss. It further relates methods of improving the appearance of hair by oral administration of an effective amount of *Stevia* extract, steviol precursors or steviol.

BACKGROUND OF THE INVENTION

*Stevia rebaudiana* is a plant which is known to contain sweet tasting compounds, including stevioside and rebaudioside A. These compounds are currently being used as sugar substitutes in a number of foodstuffs, including soft drinks A detailed report regarding their safety, toxicology and metabolism may be found in *Food and Chemical Toxicology* 2008 vol 46(7), Supplement 1, where the entire supplement is devoted to rebaudioside A as used in food and beverages. Stevioside and rebaudioside A are metabolized into the aglycone steviol, a compound which is not sweet.

JP 10265347 (Shiseido Co., Ltd) describes an agent which prolongs the growth period of the hair cycle and can be made from a number of plant extracts, including comfrey (*Symphytum officionale L.*), *Curcuma domestica*, jujube tree (*Zizyphus jujube*), Keirin wild ginger (*Asarum sieboldii*), coix seed (*Coix lachryma*), *Stevia*, cube gambir (*Uncariagambir roxburgh*), gentian (*Gentiana lutea*), hops (*Humulus lupus*), *Isodon japonicus*, and azuki bean (*Azukia angularis*), in addition to a number of other plants.

EP 1 666 036 discloses a hair growth stimulant containing a chromene compound, such as methylripariochromeme A, acetovanillochromene, or orthochromene. Chromene compounds may be extracted from some *Stevia* species, in addition to other plant genera and species. Chromenes are not structurally related to steviosides or steviol.

There is a need in the art for a hair care composition which can enhance the natural health and beauty of the hair, which can restore hair growth and prevent hair loss/thinning due to aging, and which can be orally ingested.

BRIEF DESCRIPTION OF THE INVENTION

It has been found, in accordance with this invention, that chronic consumption of an oral composition comprising steviol, a steviol precursor (steviol glycoside), or a *Stevia* extract, preferably one which contains stevioside and/or rebaudioside A (both of which are metabolized physiologically into steviol by the mammalian intestinal tract), has the surprising benefit of improving the overall appearance of hair/fur.

Thus one embodiment of this invention is a method of enhancing the overall appearance of an animal's hair/fur/feathers/scales comprising administering an oral nutraceutical or food composition comprising steviol, a steviol precursor, such as a steviol glycoside, or a *Stevia* extract which contains stevioside and/or rebaudioside A for a time sufficient and in an amount effective to enhance the overall appearance of an animal's hair/fur/feathers/scales, and observing or appreciating the result.

Another embodiment of this invention is the use of steviol, a steviol precursor such as a steviol glycoside, or a *Stevia* extract which contains stevioside and/or rebaudioside A in the manufacture of an oral nutraceutical or food composition which enhances the overall appearance of an animal's hair/fur/feathers/scales, and especially a mammal's hair/fur.

It has also been found that chronic oral supplementation with steviol restored the natural dark color of fur in old mice, which naturally develop grey fur with age. Thus another aspect of this invention is a method for restoring hair/fur color and/or delaying the onset of greyness in hair/fur comprising administering an effective amount of an oral formulation of steviol, and observing the restoration of hair/fur color, and the delayed onset of greyness in hair/fur. Yet another aspect of this invention is the use of steviol to make a nutraceutical or food composition which delays the onset of greyness and/or restores hair/fur color.

It was also found, according to this invention, that mammals ingesting steviol or *Stevia* extract which contains stevioside and/or rebaudioside A had less hair loss than animals receiving placebo. Thus another aspect of this invention comprises a method of:
  lessening hair loss,
  restoring hair growth after the onset of baldness has occurred,
  increasing the thickness of hair,
  counteracting age-associated hair thinning,
  preventing or counteracting premature hair loss,
  delaying the onset or severity of age-associated hair loss, and/or
  delaying the onset or severity of hair thinning
comprising administering an oral formulation of steviol, a steviol precursor, or a *Stevia* extract which contains stevioside and/or rebaudioside A. In yet another aspect of this invention, steviol, a steviol precursor, or a *Stevia* extract which contains stevioside and/or rebaudioside A is used in a cosmetic oral composition for the above advantages involving hair loss/thinning.

The compositions according to the invention are especially attractive, since many people, including animal owners and handlers, have a special interest in cosmetic treatments considered as "natural" with mild effects and without major side effects. As orally available compounds, *Stevia* extract and steviol have further advantages in that they are easy to use, do not leave any residue on the hair or fur, and dosages are easier to control than in topical formulations.

Figure 1:
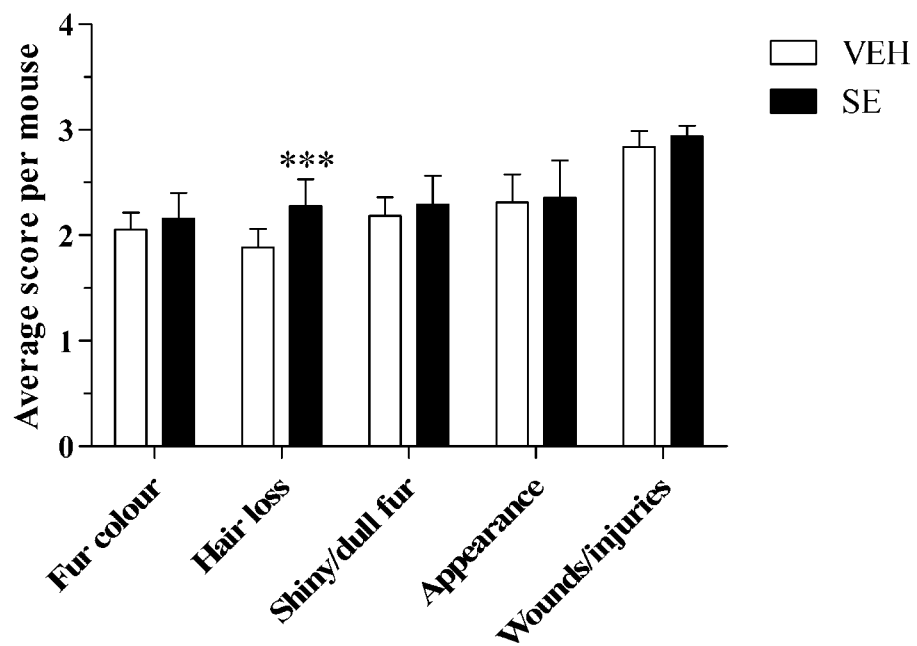
FIG. 1 Effects of chronic *Stevia* extract treatment (450 mg/kg, p.o., 8 weeks) on hair loss in middle-aged C57B1/6J mice. Data are shown as mean±S.D., the average score per mouse being displayed for *stevia* extract-treated (SE; n=12) and vehicle-treated control mice (VEH; n=13). *Stevia* extract significantly improved (i.e. reduced) hair loss, compared with control mice: ***$p<0.001$.

*Stevia* extract which contains stevioside and/or rebaudioside A, as used in this invention, may be produced using known methods. This invention is specifically not intended to include the use of *Stevia* extract as a sweetening agent for compositions where an ingredient other than *Stevia* extract, stevioside, rebaudioside A and/or rebaudioside is used to promote the enhancement of hair/fur appearance or growth. Further, the *Stevia* extract of this invention does not contain a bioactive amount of chromenes which is in an amount sufficient to impart an hair growth promoting activity.

Steviol may be obtained by enzymatic hydrolysis of stevioside according to methods described in the literature. Alternatively, since steviol glycosides, such as stevioside and rebaudioside A, are metabolized into steviol, a plant extract containing rebaudiosides and/or steviosides can be used. Preferably, the amount of steviol glycosides is high (>50%). However, these compositions have a very sweet flavor and an aftertaste, so if used in foodstuffs, it is desirable to add a taste masking or taste-enhancing substance.

As an alternative to a plant extract, compositions containing the active ingredients stevioside or rebaudioside A may also be used. Alternatively, and in particular if the hair-improving active compound is to be supplied with food and a sweet taste is not wanted, compositions containing steviol may be used. For applications involving hair coloration, steviol is particularly preferred.

DEFINITIONS

The term "nutraceutical composition" as used herein includes food products, foodstuffs, dietary supplements, nutritional supplements or a supplement composition for a food product or a foodstuff, including beverages (e.g., but not limited to, sports beverages, functional waters, juices, smoothies; instant drinks), soups, dairy products (e.g., but not limited to, single shot yogurt drinks), nutritional bars, and spreads.

As used herein, the term "food product" refers to any food or feed suitable for consumption by humans or animals.

The term "dietary supplement" refers to a small amount of a compound for supplementation of a human or animal diet packaged in single or multiple dose units. Dietary supplements do not generally provide significant amounts of calories but may contain other micronutrients (e.g. vitamins or minerals).

The term "nutritional supplement" refers to a composition comprising a dietary supplement in combination with a source of calories. In some embodiments, nutritional supplements are meal replacements or supplements (e.g. nutrient or energy bars or nutrient beverages or concentrates).

"Preventing" as used herein is not intended to mean that the event will never occur, but means delaying the onset of the condition or event, and lessening the severity of the condition or event when it does occur.

"Chronic administration" is meant to convey that administration of the active ingredient regularly occurs over an extended period of time, for example once or twice per day for a time of at least about two weeks, preferably for at least one month, and more preferably at least two months. Alternatively, the regular administration can be every two days, every three days, or once per week or twice per week.

"Hair" means both hair of a human being and animal fur. It also can include bird feathers and fish scales.

"Extended period of time" means substantially daily for a period of time of at least about two weeks, preferably at least about a month, and even more preferably for at least about two months.

"Steviol precursor" means a steviol glycoside that can be enzymatically hydrolyzed to the free aglycone steviol. See, e.g. EFSA Journal 2010, 8(4): 1537, which is hereby incorporated by reference. Enzymes suitable for this hydrolysis are present in certain microbial organisms, also present in the human or animal intestinal tract. See, e.g. Gardana et al 2003 *J. Agric. Food Chem.* 51:6618-22, which is hereby incorporated by reference.

"*Stevia* extract" as used throughout this specification and claims, it is to be understood that the extract is used as an active hair-enhancing ingredient. Thus, it is either present as the sole active appearance-enhancing ingredient, or if used in combination with another ingredient, its purpose is not that of a sweetener, and/or the amount of the *Stevia* extract is not the amount known to be used for the purpose of sweetening a composition or foodstuff, nor does it contain chromenes in an amount where they have hair growth promoting bioactivity.

"Observing" or "appreciating" may be done by either the individual who ingests the active ingredient, or may be done by a third party. The post-administration condition may be compared with the pre-administration condition and analyzed either using a standard test, or by subjective analysis.

"Enhanced Appearance" means that the hair/fur has improved at least one of the following qualities:
   Color (i.e. retention/restoration of natural color vs. greyness),
   Hair/fur alopecia (i.e. hair/fur is retained, hair loss is stopped or slowed; or hair is re-growing)
   Hair/fur thickness (progression of hair thinning is slowed, halted, or reversed)
   Fur grooming (fur no longer appears neglected, and looks better groomed)
   Skin wounds/injuries are healing or healed
   Hair/fur shininess or glossiness (hair/fur appears less dull and more shiny/glossy)
   Anti-Greying More particularly, the present invention relates to the use of oral steviol or steviol-precursor-containing compositions in hair care, particularly for the prevention of the greying of hair and/or for restoration and/or maintenance of the natural hair colour. It also relates to orally administered hair care compositions, particularly for the prevention of the greying of hair and/or for restoration and/or maintenance of natural hair colour comprising a *Stevia* extract or steviol or steviol precursor and a carrier conventionally used for oral nutraceutical or food compositions, with the proviso that if present in combination with a second active ingredient, the *Stevia* extract is not present in an amount suitable for the purpose of sweetening the composition. Furthermore, the invention relates to a method of preventing the greying of hair and/or restoring and/or maintaining the natural hair colour which comprises administering orally to a mammal in need of such treatment a composition comprising an effective amount of *Stevia* extract, steviol, or steviol precursor and observing the prevention of greying and/or restoring and/or maintaining the natural hair colour, with the proviso that if present in combination with a second active ingredient, the *Stevia* extract is not present for the purpose of sweetening the composition. For these methods and uses steviol is especially preferred.

Veterinary Uses

In another aspect of this invention, the *Stevia* extract is administered to a non-human animal, which is preferably a mammal. Since keratinaceous compounds in the hair benefit from this invention, the benefits of this invention are not limited to mammals, and may be extended to other animals such as birds, or fish, or other animals where coloration or appearance quality is of interest. For example, the bird may be poultry, especially ones which are entered in show competitions. Fish, for example koi and the like, can also benefit from enhanced coloration.

In a preferred aspect of this invention, the non-human animal is a mammal, such as a companion animal (dog, cat, ferret) or an animal which is used in the fur industry (minks, chinchillas or the like), or an animal which is shown in competition (such as dogs, horses, cats, rabbits and other farm animals). Supplementing the animal's diet with the *Stevia* extract, steviol, or steviol precursor-containing compositions of this invention will enhance the appearance of the animals' fur. Thus another aspect of this invention is a veterinary nutraceutical or foodstuff containing a fur-enhancing amount of *Stevia* extract, steviol or steviol precursor.

As some animals may not like the taste of the sweet *Stevia* extract, for veterinary uses, it may be preferred that the extract contains steviol rather than steviol precursors, as steviol does not have a distinctive taste.

Another aspect of this invention is a supplement especially designed for a show animal which comprises *Stevia* extract, steviol, or steviol precursor. The animal should be fed this supplement daily for at least one month, and preferably for at least two months prior to the competition in order for its fur to be at its optimal condition. In preferred embodiments, the supplement is in the form of a treat or chew.

Preferred Food Products

The food product may be a prepared and packaged food (e.g. mayonnaise, salad dressing, bread, or cheese food) or an animal feed (e.g. extruded and pelleted animal feed, coarse mixed feed, pet food composition, treats or chews).

Food products or foodstuffs are, for example, beverages such as non-alcoholic and alcoholic drinks as well as liquid preparations to be added to drinking water and liquid food. Non-alcoholic drinks are for instance: soft drinks, sport drinks, fruit juices, (e.g. orange juice, apple juice and grapefruit juice); lemonades, teas, near-water drinks, milk and other dairy drinks (e.g. yoghurt drinks) and diet drinks. In another embodiment, food products or foodstuffs refer to solid or semi-solid foods comprising the composition according to the invention. These forms can include, but are not limited to, baked goods such as: cakes and cookies, puddings, dairy products, confections, snack foods, or frozen confections or novelties (e.g. ice cream, milk shakes), prepared frozen meals, candy, snack products (e.g. potato crisps/chips), liquid food such as soups, spreads, sauces, salad dressings, prepared meat products, cheese, yogurt and any other fat- or oil-containing foods, and food ingredients (e.g. wheat flour).

Animal feed, including pet food compositions, advantageously include food intended to supply necessary dietary requirements, as well as treats (e.g. dog biscuits) or other food supplements. The animal feed comprising the composition according to the invention may be in the form of a dry composition (e.g. kibble), semi-moist composition, wet composition, or any mixture thereof. Alternatively or additionally, the animal feed is a supplement, such as a gravy, drinking water, yogurt, powder, suspension, chew, treat (e.g. biscuits) or any other delivery form.

Dietary supplements of the present invention are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard (shell) gelatine capsule. Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation and administration may be found in the latest edition of *Remington's Pharmaceutical Sciences* (Maack Publishing Co., Easton, Pa.).

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food, e.g. enclosed in caps of food or beverage containers for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colourants, sweeteners, flavourants, inert ingredients, and the like.

In some embodiments, the dietary supplements further comprise vitamins and minerals including, but not limited to, calcium phosphate or acetate, tribasic; potassium phosphate, dibasic; magnesium sulphate or oxide; salt (sodium chloride); potassium chloride or acetate; ascorbic acid; ferric orthophosphate; niacinamide; zinc sulphate or oxide; calcium pantothenate; copper gluconate; riboflavin; beta-carotene; pyridoxine hydrochloride; thiamine mononitrate; folic acid; biotin; chromium chloride or picolonate; potassium iodide; sodium selenate; sodium molybdate; phylloquinone; vitamin D3; cyanocobalamin; sodium selenite; copper sulphate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g. energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex; e.g. sucrose, maltodextrins, and uncooked cornstarch).

Sources of protein to be incorporated into the nutritional supplement of the invention can be any suitable protein utilised in nutritional formulations and can include whey protein, whey protein concentrate, whey powder, egg, soy flour, soy milk, soy protein, soy protein isolate, caseinate (e.g. sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See *Modern Nutrition in Health and Disease*, Eighth Edition, Lea & Febiger, publishers, 1986, especially Volume 1, pages 30-32.

The nutritional supplement can also contain other ingredients, such as one or a combination of other vitamins, minerals, antioxidants, fibre and other dietary supplements (e.g. protein, amino acids, choline, lecithin, omega-3 fatty acids). Selection of one or several of these ingredients is a matter of formulation, design, consumer and end-user preference. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulphate or oxide; salt (sodium chloride); potassium chloride or acetate; ascorbic acid; ferric orthophosphate; niacinamide; zinc sulphate or oxide; calcium pantothenate; copper gluconate; riboflavin; beta-carotene; pyridoxine hydrochloride; thiamine mononitrate; folic acid; biotin; chromium chloride or picolonate; potassium iodide; sodium selenate; sodium molybdate; phylloquinone; vitamin D3; cyanocobalamin; sodium selenite; copper sulphate; vitamin A; vitamin C; Vitamin E, inositol; and potassium iodide. Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavours, colouring agents, spices, nuts and the like may be incorporated into the nutraceutical composition. Flavourings can be in the form of flavoured extracts, volatile oils, chocolate flavourings, peanut butter flavouring, cookie crumbs, crisp rice, vanilla or any commercially available flavouring. Examples of useful flavourings include, but are not limited to: pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as lemon oil, bay oil, bergamot oil, cedarwood oil, walnut oil, cherry oil, cinnamon oil, clove oil, or peppermint oil; peanut butter, chocolate flavouring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g. from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, such as, but not limited to: saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycaemia.

Dosages

For human and animal use, the recommended dosage for *Stevia* extract is in the range of 0.1 to 500 mg/kg body weight per day; preferably from 0.5 to 250 mg/kg body weight per day; and more preferably from 1.0 to 50 mg/kg body weight per day.

For steviol, the preferred dosages range from 0.01 to 100 mg/kg body weight per day, preferably 0.1 to 50 mg/kg body weight per day, and more preferably from 0.5 to 25 mg/kg body weight per day, and/or 0.5 to 10 mg/kg body weight per day.

For steviol precursors, the preferred dosages range from 0.05 to 1000 mg/kg body weight per day, preferably from 0.5 to 500 mg/kg body weight per day; and more preferably from 1.0 to 100 mg/kg body weight per day.

The preferred daily dosage of the subject composition as specified above may be administered in the form of one or more dosage units such as, e.g., a tablet. Most preferably the daily dosage of the subject composition is provided in the form of one dosage unit taken twice daily, for a total of two dosage units a day, or in the form of two dosage units taken twice daily, for a total of four dosage units a day. Compared to taking the total daily dose once a day, twice daily dosing of half the total daily dose in one or more dosage units per dose provides improved absorption and better maintenance of blood levels of the essential ingredients. For *Stevia* extract or precursors of steviol, the dosage per dosage unit ranges from 30-1000 mg; for steviol it ranges from 10 to 500 mg.

For human and animal use, the recommended dosage for steviol glycosides is in the range of 0.05 mg per kg body weight to about 100 mg per kg body weight per day. More preferred is a daily dosage of about 0.1 to about 20 mg per kg body weight, and especially preferred is a daily dosage of about 1.0 to 10.0 mg per kg body weight.

Recommended Levels in Foodstuffs

| Food Category | Steviol precursor (steviol glycoside, e.g. Rebaudioside A or stevioside) mg/kg food | Steviol precursor (steviol glycoside) mg per dose | Free steviol mg/kg food | Free steviol per mg dose |
|---|---|---|---|---|
| Cereals (oatmeal, cold cereal, cereal bars) | 50-1000 | 2-40/40 g | 250-750 | 10-30/40 g |
| Ready-to-drink teas | 20-480 | 5-120/0.25 L | 20-200 | 5-50/0.25 L |
| Fruit juice drinks | 50-600 | 12.5-150/0.25 L | 30-200 | 5-100/0.25 L |
| Diet soft drinks | 50-600 | 12.5-150/0.25 L | 30-200 | 5-50/0.25 L |
| Energy drinks | 50-600 | 12.5-150/0.25 L | 120-600 | 30-150/0.25 L |
| Flavored waters | 20-400 | 5-100/0.25 L | 20-1200 | 5-30/0.25 L |
| Fine bakery products | 50-1000 | 2-40/40 g | 250-750 | 10-30/40 g |
| Confectionary, candy | 1000-6000 | 20-120/20 g | | 5-20/20 g |

In a preferred embodiment, the *Stevia* extract- or steviol- or steviol-precursor-containing nutraceutical or food is eaten on a regular basis, i.e. at least daily for a sustained period of time (i.e. at least one week, preferably at least two weeks, and more preferably for at least three weeks, or at least one or two months) until the hair enhancement is noted. After this time, the consumer may choose to lessen the dosage.

The following non-limiting examples are presented to better illustrate the invention.

EXAMPLE 1

Effects of Chronic *Stevia* Extract Treatment on Fur and Skin Condition in Middle-Aged Wild-Type Mice Middle-aged C57B1/6J mice (18 months of age) were administered *Stevia* extract (450 mg/kg, p.o.) or vehicle (water/corn oil, 1:1 mixture) daily, for eight weeks. At the end of the treatment period, mice were anaesthetized (2.2-2.4% isofluorane) and photographs were taken of each mouse. Eight participants, with extensive experience of performing experimental studies using mice, were asked to subjectively rate the condition of the fur and skin of each mouse, according to a three-point scale (see Table 1). The parameters rated for fur condition included fur colour, hair loss, "shininess" (glossiness) and general appearance (groomed/non-groomed); for skin condition, participants were requested to rate the appearance of wounds. The average score for each mouse, derived from the eight respondents' individual ratings, enabled subsequent comparison between *Stevia* extract-treated mice and vehicle-treated control mice.

As can be seen in FIG. 1, *Stevia* extract treatment significantly reduced the degree of hair loss, in comparison with control mice, as demonstrated by higher subjective rating scores for this parameter (p<0.01; unpaired t-test).

TABLE 1

| Fur and skin condition rating system. | | |
|---|---|---|
| Fur colour: | | |
| Grey and old 1 ☐ | Not obvious 2 ☐ | Dark and young 3 ☐ |
| Baldness/hair loss: | | |
| Lots of hair loss 1 ☐ | Some hair loss 2 ☐ | Normal hair 3 ☐ |
| Shiny fur: | | |
| Dull fur 1 ☐ | Not obvious 2 ☐ | Shiny and healthy 3 ☐ |

TABLE 1-continued

| Fur and skin condition rating system. | | |
|---|---|---|
| Appearance of fur: | | |
| Neglected and scrubby 1 ☐ | Not obvious 2 ☐ | Well-groomed 3 ☐ |
| Conspicuous wounds/injuries: | | |
| Many 1 ☐ | Few 2 ☐ | None 3 ☐ |

EXAMPLE 2

Effects of Chronic Steviol Treatment on Fur and Skin Condition in Aged Wild-Type Mice Female, aged, C57B1/6J mice (22-24 months of age) were assessed for their fur quality at the start and end of a six-week study. Prior to commencement of treatment, photographs were taken of all mice whilst under light anaesthesia (2.2-2.4% isofluorane). Mice were then fed either placebo diet or diet supplemented with steviol (120 mg/kg/d) for six weeks. At the end of the six week treatment phase, mice were again anaesthetised and further photographs were taken.

Eleven participants with extensive experience of performing experimental studies using mice were asked to complete the same questionnaire (see Table 1), to enable subjective rating of a number of parameters of fur quality and of the appearance of skin wounds, by assessing the photographs taken before and after treatment.

Statistical analyses were performed using Prism 5 (GraphPad Software, La Jolla, Calif., USA) and comprised two-way ANOVA (test factors: Time and Treatment), followed by Bonferroni post-hoc tests, where appropriate.

Figure 2:
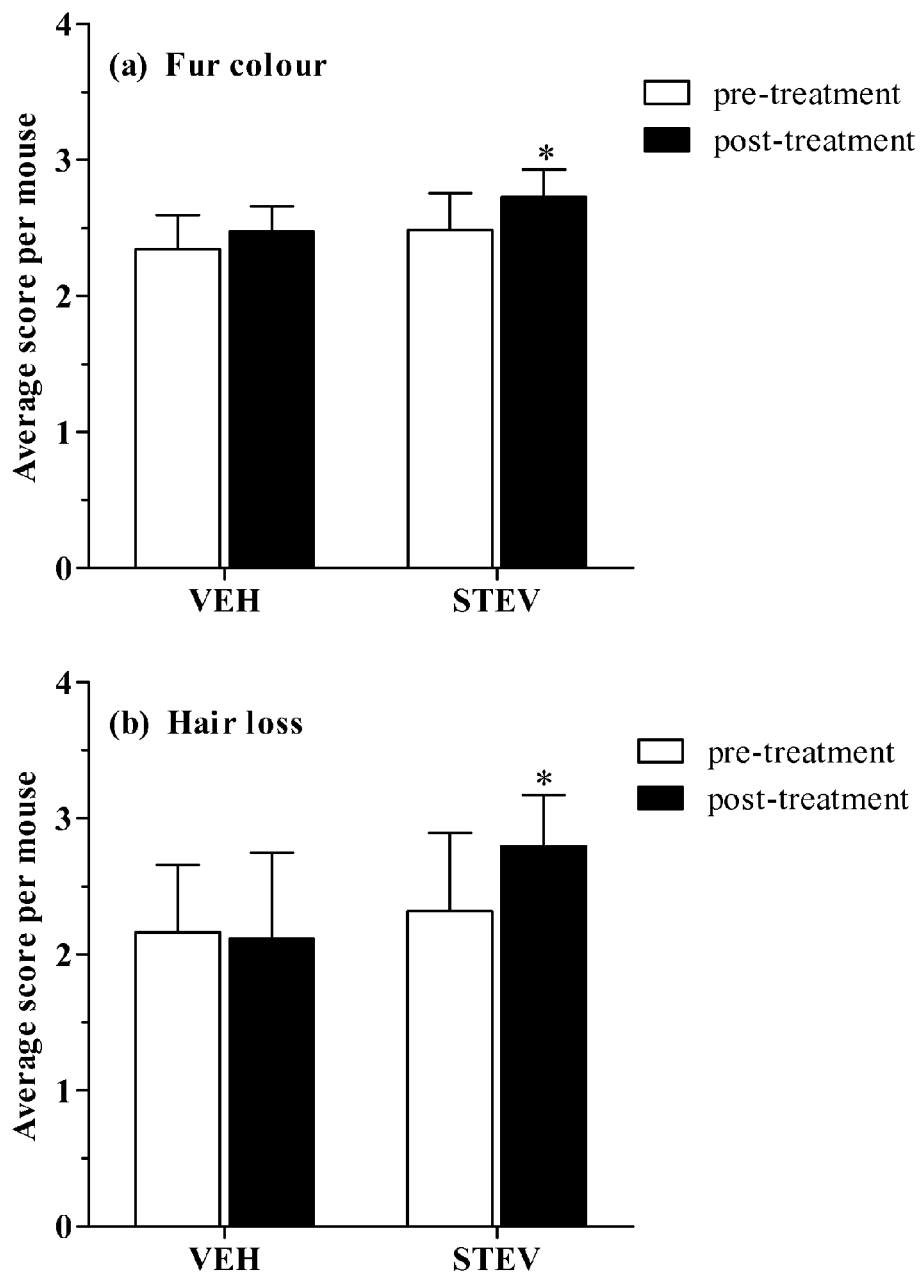
FIG. 2 Effects of chronic steviol treatment (120 mg/kg, p.o., 6 weeks) on (a) fur colour and (b) hair loss in aged C57B1/6J mice. Data are shown as mean±S.D., the average score per mouse pre- and post-treatment being displayed for steviol-treated mice (STEV; n=7) and vehicle-treated control mice (VEH; n=10). Steviol significantly improved hair colour (i.e. reduced greying) and significantly improved (i.e. reduced) hair loss (pre- vs. post-treatment: *p<0.05).

Steviol significantly improved fur colour, i.e. reduced greying, as indicated by a significantly higher average score following 6 weeks' steviol supplementation (p<0.05; FIG. 2a). In addition, steviol supplementation resulted in a significant reduction of hair loss, as indicated by a significantly higher post-treatment score (p<0.05; FIG. 2b).

Mice were sacrificed immediately after being photographed, and blood was collected.

EXAMPLE 3

Correlation Between Plasma Levels of Free Steviol and the Phenotypic Rating

Plasma samples were stored at −80° C. until the samples were removed for extraction and sample preparation. The "free" (aglycone) analytes were extracted from the plasma/serum sample with extraction buffer (50 uL ammonium acetate (10 mM) added to 400 uL ethyl acetate). The organic phase was evaporated and the dried residue was reconstituted in the mobile phase. Chromatographic separation was performed by an Agilent quadrupole mass spectrometer equipped with an 1100 Agilent LC system on an RP-Amide-column (3 um, 100×2.1 mm) in the gradient mode (A: 20 mM ammonium acetate and 0.1% acetic acid in water, B: 0.1% acetic acid in acetonitrile; 20%B (stay 2 min) to 100%B in 18 min (stay 2 min), then post-run 2 min, run time 24 min. Mass spectrometric detection was carried out with negative electrospray ionization in the SIM-mode (317 m/z). The identification and quantification were performed using steviol reference standards.

Figure 3:
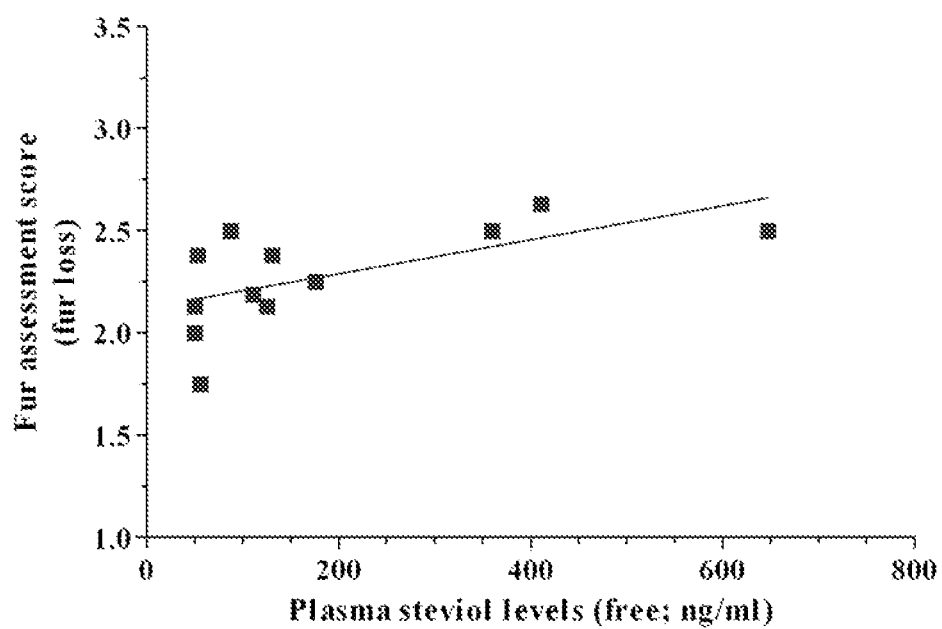
FIG. 3 shows the correlation between plasma levels of free steviol and the phenotypic rating showing a prevention of hair loss given in Example 1.

The correlation between plasma steviol concentrations and phenotypic improvement was assessed using Prism 5 (GraphPad Software, La Jolla, Calif., USA). Results are shown in FIG. 3.

EXAMPLE 4

Growth of Human Hair Follicle

Human hair follicles were obtained from human skin fragments (obtained by plastic surgery) and grown in supplemented William's E medium supplemented with penicillin/streptomycin, L-glutamine (2 mM/L), insulin (10 μg/mL and hydrocortisone (8 nM/L). Hair follicle growth was assessed via length measurements (days 0, 4, and 7). Triiodothyronine (T3, 30 μM/L) was used as positive control. The effect of steviol (at 0.625-5 μg/mL) was tested in parallel. On day 7, RNA was extracted from hair follicles that had been subjected to different treatments (control, T3, steviol). RNA was processed for Affymetrix® DNA microarray analysis in order to identify effects of compounds on gene expression. Where appropriate, RNA expression levels were further quantified by RT-PCR using the ABI 7900 Taqman instrumentation. In all procedures the protocols suggested by the manufacturers were strictly followed.

Results

Effects on Hair Follicle Growth:

Steviol dose-dependently favoured the elongation of hair follicles (Table 2, below). At low concentrations the effect was significant, whereas at higher concentrations the compound did not significantly contribute to growth.

TABLE 2

| Treatment | Concentration | Growth (% of control) | p-value |
|---|---|---|---|
| Control | | 100 | — |
| Triiodothyronine | 30 μM | 133 | <0.01 |
| Steviol | 0.625 μg/mL | 122 | <0.1 |
| Steviol | 1.25 μg/mL | 121 | <0.1 |
| Steviol | 2.5 μg/mL | 113 | Not significant |
| Steviol | 5 μg/mL | 117 | Not significant |

Effect on Gene Expression:

Global effects of steviol on gene expression were determined by transcriptomics i.e. DNA microarray analysis. The obtained data were processed with Genedata software tools. This resulted in a list of genes that had significantly different expression levels in steviol-treated hair follicles (compared to untreated hair follicles). Examples of genes that were differentially up-regulated by steviol and which are involved in epidermal physiology are given in Table 3. Only genes directly or indirectly involved in epidermal proliferation or differentiation and which were at least 2-fold up-regulated are listed. Thus another aspect of this invention is a method of up-regulating at least one of the genes listed in Table 3 comprising administering steviol and observing a hair growth effect.

TABLE 3

| Gene | Ratio of steviol-treated/untreated | p-value |
|---|---|---|
| Transmembrane protein with EGF-like and two follistatin-like domains 2 | 3.10 | 0.0001 |
| Fibroblast growth factor 7 (keratinocyte growth factor) | 2.91 | 0.0006 |
| CASP8 and FADD-like apoptosis regulator | 2.58 | 0.0004 |
| Topoisomerase (DNA) II alpha 170 kDa | 2.45 | 0.0004 |
| TIMP metallopeptidase inhibitor 3 | 2.32 | 0.0001 |
| Chemokine (C-X-C motif) ligand 12 (stromal cell-derived factor 1) | 2.22 | 0.0005 |
| Integrin, alpha 6 | 2.15 | 0.0004 |
| Collagen, type IV, alpha 6 | 2.04 | 0.0008 |
| Insulin-like growth factor 1 receptor | 2.00 | 0.001 |

Figure 4:
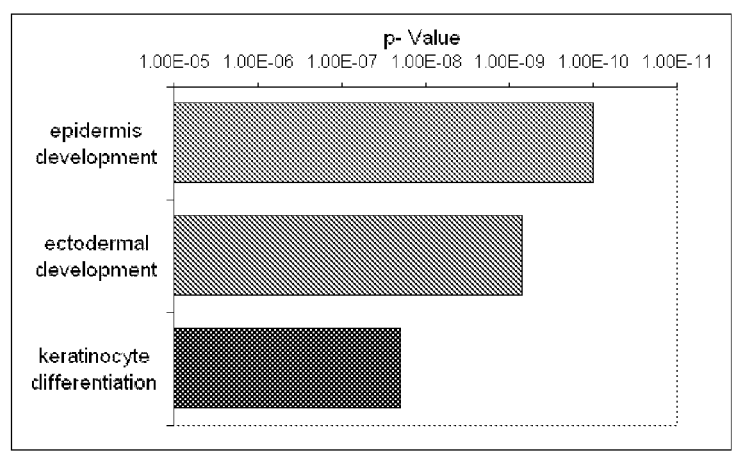
FIG. 4 shows the genes regulated by steviol which were further mapped to biological pathways using statistical tools provided with the Genedata software package.

The genes regulated by steviol were further mapped to biological pathways using statistical tools provided with the Genedata software package (FIG. 4): steviol modulated gene expression of the pathways of epidermal development, ectoderm development and keratinocyte differentiation with a high statistical significance (indicated by p-value in Table 3); other pathways were not significantly affected. This data are in line with the observed effect of steviol on hair follicle elongation (see Table 2) and corroborate that steviol modulates molecular pathways that lead to changes in hair growth.

The mRNA level of some marker genes involved in growth and/or differentiation of cells in the skin and in hair follicle was further determined by RT-PCR and is shown in Table 4.

TABLE 4

| Gene | Treatment of human hair follicle (concentration) | Fold changes (versus control) |
|---|---|---|
| All genes | Control (untreated) | 1 |
| Keratin 6 | Steviol (10 μg/mL) | 1.33 ± 0.11 |
| COX-2 | Steviol (1.25 μg/mL) | 0.46 ± 0.17 |
| Integrin alpha-6 | Steviol (0.625 μg/mL) | 1.62 ± 0.06 |
| HO-1 | Steviol (1.25 μg/mL) | 0.64 ± 0.08 |
| Involucrin | Steviol (1.25 μg/mL) | 0.51 ± 0.22 |

The importance of these genes in epidermal and therefore also hair development is described and discussed in detail e.g. by Adriani et al. *J. Invest Dermatol* 120: 923-931 (2003); Grochot-Preczek et al. *Thromb Haemost* 104 (on-line 10—June 2010); Li et al. *Exp Dermat* 9: 431-438 (2000); Ma et al. *Ann Acad Med Singapore* 33: 784-8 (2004); Neufang et al. *Proc Nat Acad Sci (USA)* 98: 7629-7634 (2001). Thus another aspect of this invention is a method of up-regulating a hair-development associatated gene selected from the group consisting of Keratin 6 or Integrin alpha-6 or both, comprising administering steviol and observing hair growth. Another aspect of this invention is a method of down-regulating COX-2 (involved in inflammation) and/or HO-1 (involved in oxidation) comprising administering comprising administering steviol and observing hair growth.

EXAMPLE 5

Effect on Mouse Skin

The effect of steviol on gene expression was also analysed in whole mouse skin (also containing hair follicles). To this aim, mice were fed a normal diet or a diet supplemented with steviol (see also relevant data above). After eight weeks of supplementation, mice were sacrificed and skin was isolated and freed from hair. Quantitative RT-PCR was performed for selected genes using the same technology as described for hair follicles (see above). Remarkably, we identified changes in expression levels of some genes that are involved in skin physiology and homeostasis. They are listed in Table 5.

The importance of these genes in skin biology have been shown by Pirilä et al. *Wound Repair & Regeneration* 151:47-57(2007); Varani et al. *Brit J Cancer* 82: 657-665 (2000); Fisher et al. *J Invest Dermatol.* 117:219-26 (2001); Kaesler et al. *Cytokine* 17: 157-163 (2002); Tanabe et al. *J Dermatol Sci* 43: 210-213 (2006); Schmutt et al. *Horm Metab Res* 39:96-105 (2007) for matrix metalloproteinases (MMP), chemokines, interleukin and PPAR, respectively.

TABLE 5

| Gene | Dietary supplementation with | % of control (based on fold-change) |
|---|---|---|
| Any gene | — | 100 |
| MMP-8 | Steviol | 73 ± 23 |
| MMP-13 | Steviol | 53 ± 9 |
| CXC10 | Steviol | 132 ± 50 |
| IL-6 | Steviol | 130 ± 31 |
| PPAR-δ | Steviol | 60 ± 37 |

MMP-8 and MMP-13 have collagenase activity. Thus, another aspect of this invention is a method of downregulating MMP-8 and/or MMP-13 comprising administering steviol, and observing enhanced hair and/or skin appearance.

EXAMPLE 6

Tablet

| | |
|---|---|
| Steviol | 150 mg |
| Microcrystalline cellulose | 300 mg |
| Lactose | 300 mg |
| Crospovidone | 10 mg |
| Mg-Stearate | 2.5 mg |
| SiO$_2$ | 2.5 mg |

Steviol, microcrystalline cellulose, and SiO$_2$ is mixed in a tumbler mixer for 10 min. Then, lactose is added and the composition is mixed for a further 10 min. Crospovidone is combined with the other ingredients and mixed for 10 min. Finally, Mg-stearate is added to the other components and mixed for another 2 min. The mixture is compressed to tablets. One tablet per day is taken in the morning with breakfast.

EXAMPLE 7

Preparation of a Hard Gelatine Capsule

| Ingredient | Amount per Capsule |
|---|---|
| Steviol | 100 mg |
| Lactose | 295 mg |
| SiO$_2$ | 5 mg |

Steviol, lactose and SiO$_2$ are mixed in a tumbler mixer for 15 minutes and then filled into capsules.

Two capsules per day for 3 months may be administered to a human adult upon hair loss. The dose can be increased on demand to up to 3 capsules per day. To support hair growth on a regular basis, or to prevent thinning and greying, 1 caspule can be taken on a regular basis.

EXAMPLE 8

Preparation of an Instant Flavoured Soft Drink

| Ingredient | Amount [g] |
|---|---|
| Steviol | 0.5 |
| Sucrose, fine powder | 763.1 |
| Ascorbic acid, fine powder | 2.0 |
| Citric acid anhydrous powder | 55.0 |
| Lemon flavour | 8.0 |
| Trisodium citrate anhydrous powder | 6.0 |
| Tricalciumphosphate | 5.0 |
| β-Carotene 1% CWS from DNP AG, Kaiseraugst, Switzerland | 0.4 |
| Total amount | 840 |

All ingredients are blended and sieved through a 500 μm sieve. The resulting powder is put in an appropriate container and mixed in a tubular blender for at least 20 minutes. For preparing the drink, 105 g of the obtained mixed powder are mixed with sufficient water to produce one liter of beverage.

The ready-to-drink soft drink contains ca. 15 mg enriched steviol extract per serving (250 ml). As a regular hair growth supporting drink, 2 servings per day (500 ml) may be drunk.

EXAMPLE 9

Preparation of a Fortified Non-Baked Cereal Bar

| Ingredient | Amount [g] |
|---|---|
| Steviol | 0.3 |
| Water | 54.0 |
| Salt | 1.5 |
| Glucose syrup | 130.0 |
| Invert sugar syrup | 95.0 |
| Sorbitol Syrup | 35.0 |
| Palm kernel fat | 60.0 |
| Baking fat | 40.0 |
| Lecithin | 1.7 |
| Hardened palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skimmed milk powder | 45.0 |
| Apple flavour 74863-33 | 2.0 |
| Citric acid | 5.0 |
| Total amount | 885 |

The enriched steviol is premixed with skimmed milk powder and placed in a planetary bowl mixer. Cornflakes and rice crispies are added and the total is mixed gently. Then the dried and cut apples are added. In one cooking pot, water and salt are mixed in the amounts given above (solution 1). In a second cooking pot, glucose-, invert sugar- and sorbitol-syrups are mixed in the amounts given above (solution 2). The fat phase constitutes a mixture of baking fat, palm kernel fat, lecithin and emulsifier. Solution 1 is heated to 110° C. Solution 2 is heated to 113° C. and then cooled in a cold water bath. Subsequently, solutions 1 and 2 are combined. The fat phase is melted at 75° C. in a water bath, then added to the combined mixture of solutions 1 and 2. Apple flavour and citric acid are added to the liquid sugar/fat mix. The liquid mass is added to the dry ingredients and mixed well in the planetary bowl mixer. The mass is put on a marble plate and rolled to the desired thickness. The mass is cooled down to room temperature and cut into pieces. The non-baked cereal bar contains ca. 10 mg steviol per serving (30 g). To support a sustained hair health and growth, 1-2 cereal bars may be eaten per day.

EXAMPLE 10

Dry Dog Feed Containing Steviol

A commercial basal diet for dogs (e.g. Mera Dog "Brocken", MERA-Tiernahrung GmbH, Marienstraβe 80-84, D-47625 Kevelaer-Wetten, Germany) is sprayed with a solution of *stevia* extract in water, together with antioxidants such as vitamin C (e.g. ROVIMIX® C-EC from DSM Nutritional Products Ltd, Kaiseraugst, Switzerland) and its derivatives, i.e. sodium ascorbyl monophosphate (e.g. STAY-C® 50 from DSM Nutritional Products Ltd, Kaiseraugst, Switzerland) or a mixture of tri-, di- and mono-phosphate esters of sodium/calcium L-ascorbate (e.g. ROVIMIX® STAY-C® 35 from DSM Nutritional Products Ltd, Kaiseraugst, Switzerland) in an amount sufficient to administer to a dog a daily dose of 4 mg steviol per kg body weight. The food composition is dried to contain dry matter of about 90% by weight. For an average dog of 10 kg body weight to consume approx. 200 g dry feed per day, the dog food contains approx. 200 mg steviol per kg food. For heavier dogs, the feed mix is prepared accordingly.

To improve the coat of a dog on a regular basis, the steviol-containing dry food is given daily. Seasonally, e.g. during wintertime, or upon specific demands, e.g. before shows, additionally treats or capsules containing steviol can be given 2-3× per day over several weeks to increase the dose.

EXAMPLE 11

Wet Cat Food Containing Steviol

A commercial basal diet for cats (e.g. Happy Cat "Adult", Tierfeinnahrung, Südliche Hauptstratβe 38, D-86517 Wehringen, Germany) is mixed with a solution of *stevia* extract in water, together with antioxidants such as vitamin C (e.g. ROVIMIX® C-EC from DSM Nutritional Products Ltd, Kaiseraugst, Switzerland) and its derivatives, i.e. sodium ascorbyl monophosphate (e.g. STAY-C® 50 from DSM Nutritional Products Ltd, Kaiseraugst, Switzerland) or a mixture of tri-, di- and mono-phosphate esters of sodium/calcium L-ascorbate (e.g. ROVIMIX® STAY-C® 35 from DSM Nutritional Products Ltd, Kaiseraugst, Switzerland) in an amount sufficient to administer to a cat a daily dose of 4 mg *stevia* extract per kg body weight. For an average cat of 5 kg of body weight to consume approx. 400 g of wet food, the cat food contains 50 mg steviol per kg food. The food composition is dried to contain dry matter of about 90% by weight. To improve the coat of a cat on a regular basis, the steviol containing dry food is given daily. Seasonally, eg during wintertime, or upon specific demands, eg before shows, additionally treats or capsules containing steviol can be given 2-3× per day over several weeks to increase the dose.

EXAMPLE 12

Dog Treats Containing Steviol

Commercial dog treats (e.g. Mera Dog "Biscuit" for dogs as supplied by Mera Tiernahrung GmbH, Marienstrasse 80-84, 47625 Kevelaer-Wetten, Germany) are sprayed with a solution of *Stevia* extract in water, together with antioxidants such as vitamin C (e.g. ROVIMIX® C-EC from DSM Nutritional Products Ltd, Kaiseraugst, Switzerland) and its derivatives, i.e. sodium ascorbyl monophosphate (e.g. STAY-C® 50 from DSM Nutritional Products Ltd, Kaiseraugst, Switzerland) or a mixture of tri-, di- and mono-phosphate esters of sodium/calcium L-ascorbate (e.g. ROVIMIX® STAY-C® 35 from DSM Nutritional Products Ltd, Kaiseraugst, Switzerland) in an amount sufficient to administer to the treats 0.5-5 mg steviol per g treats. The food composition is dried to contain dry matter of about 90% by weight. To reduce baldness and greying, treats can be given 2-3× per day, either alone or in addition to daily regular chow containing steviol. This can also be done before shows to increase the dose and prepare for a shiny glossy coat.

EXAMPLE 13

Cat Treats Containing *Stevia* Extract

Commercial cat treats (e.g. Whiskas Dentabits for cats as supplied by Whiskas, Masterfoods GmbH, Eitzer Str. 215, 27283 Verden/Aller, Germany) are sprayed with a solution of *Stevia* extract in water, together with antioxidants such as vitamin C (e.g. ROVIMIX® C-EC from DSM Nutritional Products Ltd, Kaiseraugst, Switzerland) and its derivatives, i.e. sodium ascorbyl monophosphate (e.g. STAY-C® 50 from DSM Nutritional Products Ltd, Kaiseraugst, Switzerland) or a mixture of tri-, di- and mono-phosphate esters of sodium/calcium L-ascorbate (e.g. ROVIMIX® STAY-C® 35 from DSM Nutritional Products Ltd, Kaiseraugst, Switzerland) in an amount sufficient to administer to the treats 0.5-5 mg *Stevia* extract per g treats. The food composition is dried to contain dry matter of about 90% by weight. Two to four treats per day can be given.

What is claimed is:

1. A method of enhancing the appearance of a mammal's hair/fur comprising administering to a mammal in need of hair/fur enhancement an oral nutraceutical or food composition comprising steviol, without chromene, for a time sufficient and in an amount effective to enhance the overall appearance of the mammal's hair/fur, and observing the enhanced appearance, wherein the enhancement of the appearance of the mammal's hair/fur is selected from the group consisting of restoring hair/fur color, lessening hair loss, increasing the thickness of hair, counteracting age-associated hair thinning, and delaying the onset or severity of age-associated hair loss and thinning.

2. A method according to claim 1, wherein the mammal is human.

3. A method according to claim 1, wherein the administration is chronic.

4. A method according to claim 1, wherein the mammal is a dog, cat, or human.

\* \* \* \* \*